United States Patent
Koenig et al.

(10) Patent No.: US 8,454,550 B2
(45) Date of Patent: Jun. 4, 2013

(54) APPARATUS FOR DETECTING MOISTURE FOR AN APPARATUS FOR MONITORING THE ACCESS TO A PATIENT, IN PARTICULAR FOR MONITORING THE VASCULAR ACCESS DURING EXTRACORPOREAL BLOOD TREATMENT

(75) Inventors: Christoph Koenig, Wiesbaden/Auringen (DE); Alexander Schroers, Frankfurt (DE); Andreas Wuepper, Buettelborn (DE); Alexander Heide, Eppstein (DE); Juergen Klewinghaus, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 106 days.

(21) Appl. No.: 13/201,593

(22) PCT Filed: Feb. 11, 2010

(86) PCT No.: PCT/EP2010/000832
§ 371 (c)(1),
(2), (4) Date: Sep. 29, 2011

(87) PCT Pub. No.: WO2010/091852
PCT Pub. Date: Aug. 19, 2010

(65) Prior Publication Data
US 2012/0029410 A1    Feb. 2, 2012

(30) Foreign Application Priority Data
Feb. 14, 2009    (DE) .................... 10 2009 008 885

(51) Int. Cl.
*A61M 37/00*    (2006.01)
(52) U.S. Cl.
USPC .......... 604/6.16; 600/371; 600/362; 604/4.01

(58) Field of Classification Search
USPC ................................................. 604/6.16, 264
See application file for complete search history.

(56) References Cited

U.S. PATENT DOCUMENTS 5,579,765 A * 12/1996 Cox et al. ...................... 600/307
5,964,703 A * 10/1999 Goodman et al. ............ 600/382
(Continued)

OTHER PUBLICATIONS

International Preliminary Report on Patentability from PCT/EP2010/000832, mailed on Aug. 16, 2011.

(Continued)

*Primary Examiner* — Tatyana Zalukaeva
*Assistant Examiner* — Jordan B Bailey
(74) *Attorney, Agent, or Firm* — Kenyon & Kenyon LLP

(57) ABSTRACT

An apparatus is disclosed for detecting moisture, which is intended for the use in an apparatus for monitoring an access to a patient for a device by means of which a fluid is conducted to and/or removed from a patient via a hose line, in particular for monitoring the vascular access during an extracorporeal blood treatment, wherein blood of a patient is removed from the patient via an arterial hose line, which has an arterial puncture cannula, and is conducted back to the patient via a venous hose line, which has a venous puncture cannula. The apparatus for detecting moisture is designed as a pad which is made of a flexible material and is to be applied onto the patient's skin and which comprises an upper side facing away from the patient's skin and a lower side facing the patient's skin. The pad comprises an opening for the passage of fluid, in particular blood, and a moisture sensor having contact elements for the connection of the same. The moisture sensor is capable of detecting blood flowing through the opening to the surface of the pad. The apparatus according to the invention is characterized in that the lower side of the pad is impervious to fluid.

32 Claims, 10 Drawing Sheets

U.S. PATENT DOCUMENTS

| | | | |
|---|---|---|---|
| 6,445,304 B1 | 9/2002 | Bandeian et al. | |
| 6,979,306 B2 * | 12/2005 | Moll | 604/4.01 |
| 7,147,615 B2 * | 12/2006 | Wariar et al. | 604/6.16 |
| 7,641,612 B1 * | 1/2010 | McCall | 600/371 |
| 2002/0137999 A1 * | 9/2002 | Bandeian et al. | 600/371 |
| 2002/0198483 A1 | 12/2002 | Wariar et al. | |
| 2005/0038325 A1 | 2/2005 | Moll | |

OTHER PUBLICATIONS

International Search Report from PCT/EP2010/000832, mailed on Jun. 14, 2010.

* cited by examiner

Fig. 2
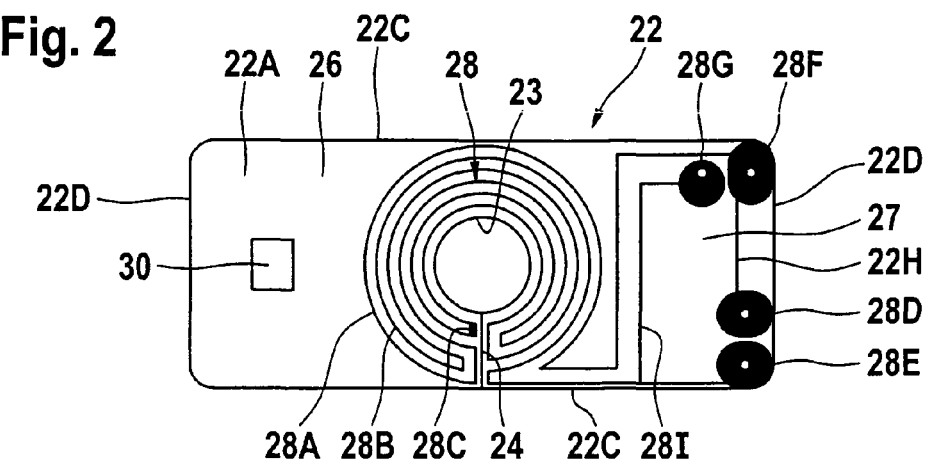
Fig. 3
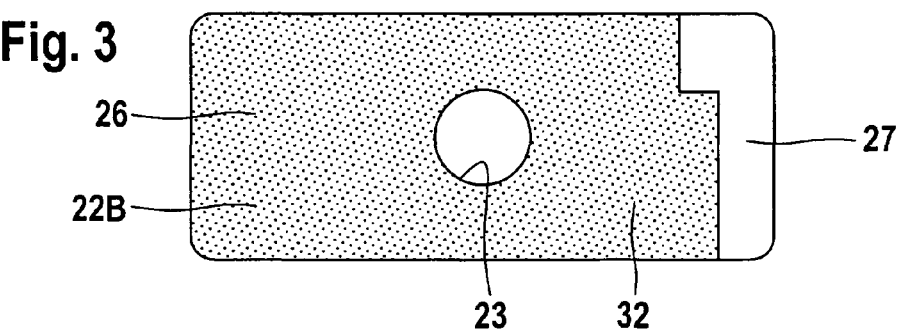
Fig. 4
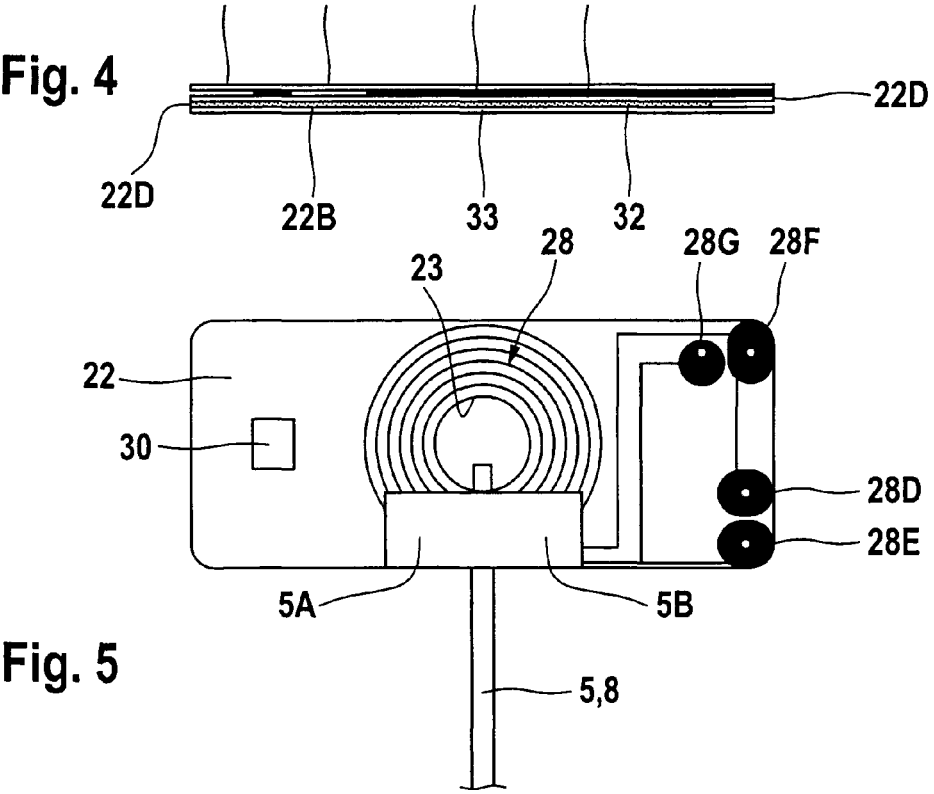
Fig. 5

APPARATUS FOR DETECTING MOISTURE FOR AN APPARATUS FOR MONITORING THE ACCESS TO A PATIENT, IN PARTICULAR FOR MONITORING THE VASCULAR ACCESS DURING EXTRACORPOREAL BLOOD TREATMENT

FIELD OF THE INVENTION

The present invention relates to a device for detecting moisture for use in a device for monitoring an access to a patient for an apparatus with which a fluid is fed to a patient and/or carried away from a patient via a hose line, in particular for monitoring the vascular access in an extracorporeal blood treatment, in which a patient's blood is carried away from the patient via an arterial hose line which has an arterial puncture cannula, and is fed back again to the patient via a venous hose line which has a venous puncture cannula. Moreover, the present invention relates to a device for monitoring an access to a patient, which comprises a device for detecting moisture. Furthermore, the present invention relates to an extracorporeal blood treatment apparatus with an extracorporeal blood circuit, which comprises an arterial hose line with an arterial cannula and a venous hose line with a venous cannula, the extracorporeal blood treatment apparatus comprising a device for monitoring the arterial and/or venous vascular access.

BACKGROUND

In the field of medical technology, a large number of apparatuses are known with which fluids can be withdrawn from patients or fluids can be fed to patients via a hose line. The access to the patient generally takes place with a catheter for introduction into body organs or a cannula for the puncturing of vessels. During examination or treatment, a proper access to the patient must be ensured. It is therefore necessary to monitor the patient access.

A proper access to the patient is also required particularly for extracorporeal blood treatment apparatuses which comprise an extracorporeal blood circuit. The known extracorporeal blood treatment apparatuses include, for example, dialysis apparatuses or cell separators, which necessitate an access to the patient's vascular system. In extracorporeal blood treatment, blood is removed from the patient with an arterial puncture cannula via an arterial hose line, the blood being fed back again to the patient with a venous puncture cannula via a venous hose line.

Despite regular monitoring of the vascular access by hospital personnel, there is in principle the risk of the puncture cannula slipping out unnoticed from the patient's blood vessel. Whereas the slipping-out of the arterial cannula is associated with the sucking-in of air into the arterial hose line, the slipping-out of the venous cannula leads to the feared free flow of blood into the surroundings. If the slipping-out of the venous cannula is not therefore detected immediately, there is a risk of the patient bleeding to death. Even if the venous cannula has not slipped out completely, there is nonetheless the risk of relatively large quantities of blood issuing at the puncture point over the whole treatment period.

Various devices of differing design are known for monitoring the vascular access. The known monitoring devices generally rely on the safety devices present as standard in blood treatment apparatuses, said safety devices triggering immediate interruption of the extracorporeal blood treatment in the case of an incorrect vascular access.

Devices for monitoring a vascular access are known, which comprise a device for detecting moisture in order to be able to detect the issuing of blood at the puncture point.

The known devices for detecting moisture for use with the known monitoring devices for a patient access are constituted as a pad which is to be placed onto the wound or puncture point. The pad is made from an absorbent material in which a moisture sensor is embedded. A drawback is that false alarms are possible, for example due to perspiration on the skin or other bodily fluids, since it is not possible to distinguish with the moisture sensor whether the moisture at the wound or puncture point can be traced back to bleeding or for example to perspiration.

A device for monitoring a patient access, which comprises a device constituted as a pad for detecting moisture, is known for example from International PCT Application Publication WO 2006/008866 A1. The known device for detecting moisture is constituted as a mat, which is placed under the patient's arm which is punctured for the access to the vascular system. The mat is composed of a plurality of layers of different materials. Embedded between the upper and lower layers is the moisture sensor, which is made from a material layer which is printed with a meandering strip conductor, the ends whereof are designed as contacts. The moisture is detected by the fact that the resistance between the contacts of the strip conductor changes. The known device seeks to overcome the problem of false alarms due to perspiration by the fact that the layer with the strip conductor is covered by a hydrophobic filter with pores. The number and size of the pores should ensure that only larger, but not smaller quantities of moisture get to the moisture sensor.

U.S. Patent Application Publication No. 2005/0038325 A1 describes a device for detecting moisture for a device for monitoring a patient access, which is constituted as a pad which is placed on the puncture point. The pad again has a multi-layer structure, the moisture sensor again being embedded between the upper and lower layers. The known device for detecting moisture is characterized in that blood issuing at the puncture point enters into the lower layer at the underside of the pad lying on the patient's skin. The sensitivity is designed to be adjusted by the distance between the moisture sensor and the lower layer, in such a way that false alarms on account of perspiration are avoided.

The pad known from U.S. Patent Application Publication No. 2005/0038325 A1 comprises a section to which the cannula is fixed. The section is separated by a predetermined rupture line from the section in which the moisture sensor is disposed. The effect of this is that, in the event of an inadvertent tug on the hose line which leads to the cannula slipping out, only the section of the pad is torn off to which the cannula is fixed, but the section with the moisture sensor remains at the puncture point. This thus ensures that an alarm is triggered even in the case of an inadvertent tug on the hose line.

A device constituted as a pad for detecting moisture, wherein the blood enters at the underside of the pad, is also known from U.S. Pat. No. 6,445,304. With a sufficient thickness of the blood-permeable porous carrier material for the moisture sensor and with a suitable spacing of the strip conductors of the moisture sensor, it is intended to avoid a false alarm being triggered by only occasional seeping of blood or small quantities of other bodily fluids.

It is also known from U.S. Pat. No. 6,445,304 to provide in a pad to be placed on the puncture point a circular cutout, from which a slit extends up to the edge of the pad. This particular design of the pad makes it possible to put the pad in place even when the patient's vascular access is already punctured with a cannula. The slit makes it possible to displace the pad from the side over the cannula which is already in place and which then extends through the circular cutout. If the pad is placed on the patient's skin before the application of the cannula, the slit does however prove to be a drawback, since the slit pad loses stability.

The problem underlying the present invention is to provide a device easy to handle for detecting moisture for use with a device for monitoring an access to a patient, wherein the risk of the occurrence of false alarms, for example due to perspiration, is reduced. Moreover, the problem underlying the present invention is to provide a device for monitoring an access to a patient, in particular for monitoring the vascular access in an extracorporeal blood treatment, said device being easy to handle and permitting a reliable detection of the issuing of blood at the puncture point. It is also a problem underlying the present invention to specify an extracorporeal blood treatment apparatus with such a device for monitoring the vascular access.

SUMMARY

According to the present invention, the solution to these problems takes place with the features described herein with regard to advantageous embodiments of the present invention.

The device according to the present invention for detecting moisture is constituted as a cover made of a flexible material to be placed on the patient's skin, said cover having an underside facing the patient's skin and an upper side facing away from the patient's skin. The cover (pad) comprises a cutout through which a cannula can be passed for the patient access, and a moisture sensor with contact elements for connection of the latter. The moisture sensor can be a disposable article or a sensor which can be used on numerous occasions.

The device according to the present invention is characterized in that the cover is not permeable to fluid at the underside. Unlike the known devices for detecting moisture, it is therefore necessary that the fluid, for example the blood at the puncture point, does not penetrate into the cover at the underside, but gets to the upper side of the cover so that it can be detected by the moisture sensor. This thus avoids only small quantities of fluids, for example perspiration, being able to penetrate from the underside into the cover and leading to false alarms.

The device according to the present invention can be used not only in blood treatment apparatuses which provide a vascular access by means of a cannula or needle, but is in principle also suitable for use in port systems and catheters.

In a preferred embodiment of the device according to the present invention, the cover impermeable to fluid at the underside is however permeable to air and water vapor at the underside. The wearer comfort of the cover according to the present invention is thus improved.

If the moisture sensor is not embedded in the cover, but is disposed on the upper side of the cover, the cover does not have to be permeable to fluid at the upper side. In a preferred embodiment, the cover is however permeable to fluid at the upper side. The cover may be constituted as a pad with two longitudinal sides and two narrow sides. The pad does not have to be essentially rectangular, but can also be essentially round or oval.

The cutout in the cover for the passage of blood is preferably an essentially circular or oval cutout. Any other shapes are, however, also possible. For example, the cutout can also be essentially square or rectangular.

The cutout in the cover makes it possible to pass the cannula through the cutout. The cannula may be applied before or after the application of the cover. It is, however, also possible to dispose the cannula beneath the cover. The cannula can then be fixed with the cover to the patient's skin.

In the case where the cannula is intended to be passed through the cutout in the cover, a particularly preferred embodiment makes provision such that the cover comprises a predetermined rupture line, which extends from the cutout in the cover to the edge of the cover. In the case where the detection device according to the present invention is placed on the patient's skin before the application of the cannula, the cover has a sufficient stability. The cannula can then be inserted through the cutout of the cover into the patient's skin. The device according to the present invention, however, also permits the user to apply the cannula first in the usual way, and then to place the cover on the patient's skin. If the user wishes to adhere to his usual sequence of operations, he merely has to tear the cover at the predetermined rupture line, so that a slit arises for the lateral introduction of the cannula into the cover as far as the cutout. The device according to the present invention can therefore be handled flexibly, but also in a straightforward manner.

The cover may have various sizes. On the one hand, it should have a sufficient size to cover the puncture point completely, but on the other hand it should not be so large that the puncture is hindered. The preferably rectangular cover preferably has a length of 8 to 12 centimeters and a width of 3 to 5 centimeters. It can also comprise one or more tabs or notches.

Since the cutout is located in the cover for the passage of blood and for the passage of the cannula, the puncture point is surrounded on all sides by the cover. The cutout should have a sufficient size, so that the passage of blood and the passage of the cannula can easily take place. When the cutout has a sufficient size, it ensures that smaller trickles of blood cannot immediately lead to an alarm, since these small quantities of blood could not then get to the surface of the cover. A sufficiently large cutout does, however, also permit the user to fix the cannula with adhesive tapes through the cutout. The diameter of the preferably circular cutout should lie between 20-35 mm.

A further preferred embodiment makes provision such that the cover comprises a flexible carrier material which may comprise one or more layers or ply. At least one strip conductor of a flexible material and at least two contact elements for the connection of the at least one strip conductor are applied on the upper side of the single- or multi-ply carrier material in order to form the actual moisture sensor.

The carrier material for the moisture sensor is preferably a medical nonwoven fabric. On account of the open structure of the nonwoven fabric, the carrier material is permeable both to air and also to water vapor, as a result of which the cover can conveniently be worn on the skin. The nonwoven fabric is biocompatible, skin-compatible, soft and flexible and may, for example, be made from a cellulose fiber/polyester fiber mixture. On account of the flexible nonwoven fabric, the cover can be adapted to any shunt geometry and can be glued onto any puncture point. The preferred thickness of the nonwoven fabric lies between 50 and 500 µm, preferably 100-200 µm, in particular 150 µm. The nonwoven fabric should preferably not have any large pores or other holes.

The maximum diameter of the pores or holes should preferably be less than 0.5 mm, so that the strip conductors applied on the carrier material are not interrupted. In order that the strip conductors cannot be torn apart, the nonwoven fabric should only be able to be stretched with relative difficulty. In the longitudinal and transverse direction, the nonwoven fabric should preferably not be able to be stretched more than 20% even with the maximum tensile forces that have to be accepted in practice.

In a particularly preferred embodiment, the strip conductors are printed onto the carrier material. Suitable printing processes are known to the person skilled in the art for the printing of the carrier material with the strip conductors. The strip conductors are preferably printed on the carrier material in the screen-printing process, since screen-printing permits the application of relatively large layer thicknesses, which are required in order to apply mechanically stable and robust strip conductors on the relatively rough, flexible and only somewhat stretchable nonwoven fabric.

In order to create the strip conductors, a paste on a silver base, bound in a thermoplastic resin, is preferably applied on the nonwoven fabric in the screen-printing process, said resin evaporating under the influence of heat during the curing. The layer thickness is not uniform on the surface of the nonwoven fabric, since the paste seeps more or less deeply into the non-homogeneous surface of the nonwoven fabric. The layer thickness of the strip conductors preferably lies between 10 μm and 150 μm.

A particularly preferred embodiment of the moisture sensor provides for a first strip conductor leading to a terminating resistor and a second strip conductor leading away from the terminating resistor, the ends of the first and second strip conductors being connected to the contact elements which are preferably printed on the carrier material. The terminating resistor is also preferably printed on the carrier material. The paste for the printed resistor preferably comprises a mixture of carbon particles and ionising particles, both bound into a thermoplastic resin which also evaporates under the influence of heat during curing.

The two strip conductors constituted as electrodes have only a low electrical resistance which lies at approximately 1 $\Omega$/cm, whereas the terminating resistor on the other hand has a high resistance, which may lie in the double- or multi-digit K$\Omega$ range. When the strip conductors are connected to one another by a liquid drop, the value of the resistance measured between the contact elements drops well below the value of the resistance of the terminating resistor. The occurrence of moisture can be detected on the basis of this change in the resistance. By means of the shape of the strip conductors and the spacing between the two strip conductors, it is possible to set the drop size from which the sensor is intended to respond.

Instead of a moisture sensor which changes its resistance as a function of the moisture, a moisture sensor known to the person skilled in the art that changes its capacitance as a function of the moisture can also be integrated into the cover.

The at least one strip conductor on the carrier material may have a differing course. The at least one strip conductor preferably forms a conductor loop at least partially surrounding the cutout in the cover. The conductor loop should be formed in such a way that it does not tear when the predetermined rupture line is torn open. The conductor loop should closely surround the cutout in the cover as far as possible on all sides.

In the particularly preferred embodiment which makes use of printed strip conductors, the carrier material preferably comprising nonwoven fabric must have properties which permit printability. Thus, the surface of the nonwoven fabric must not be hydrophobic, for example in the case of a printing ink on a water base. The nonwoven fabric must also be able to withstand the exposure required for drying of the printing paste or ink, for example the heat or UV radiation.

The printing paste or ink for the strip conductors or contact elements can also be used to print other lettering or markings on the cover which can give the user special instructions for handling.

In a further particularly preferred embodiment, the cover comprises a predetermined rupture line dividing the cover into two sections, the moisture sensor being disposed in one of the two sections of the cover. The puncture cannula may be fixed to the other part of the cover. In the case where the puncture cannula is torn out, only the section to which the cannula is fixed is torn away from the cover. This ensures that the other section in which the moisture sensor is located remains on the patient's skin.

The section of the cover to which the cannula is fixed may be constituted in different ways. It may form a sub-zone of the cover, i.e., be surrounded laterally by the other section, or be constituted as a strip projecting outwards as a tab. The only crucial factor is that this section can easily be detached from the other section when the section for fixing the cannula is subjected to tensile load.

A further particularly preferred embodiment provides for a third strip conductor leading to a second terminating resistor and a fourth strip conductor leading away from the second terminating resistor, the ends of the third and fourth strip conductors being connected electrically to the contact elements which are applied on the carrier material. A parallel connection of two resistors is thus created. In this embodiment, it is possible to dispose the second predetermined rupture line, which separates the first from the second section of the cover, in such a way that it runs either through the first and/or second strip conductor or through the third and/or fourth strip conductor. The effect of this is that, when the needle is torn away, only the first and/or second strip conductor or the third and/or fourth strip conductor is severed, and this leads to a corresponding change in the total resistance of the parallel connection of the two terminating resistors. Tearing-away of the cannula therefore does not lead to complete destruction of the moisture sensor. When the change in the resistance is monitored, it is possible to detect immediately that the cannula has been torn away. It is possible from the amount of the change in resistance to distinguish whether the cannula has been torn away or bleeding has occurred.

In a further preferred embodiment, the cover is constituted as an adhesive plaster which has an adhesive layer at its underside. This adhesive layer may be covered by a cover layer, for example a film or a paper, which is pulled off before the application of the cover on the patient's skin. The adhesive layer preferably extends only over one section of the underside of the cover, so that the other section of the cover at the underside is free from the adhesive layer. This part of the cover free from the adhesive layer is intended for the application of the contact elements of the moisture sensor. Since the section with the contact elements of the moisture sensor does not adhere to the patient's skin, a suitable plug can easily be fixed to the cover even when the section with the adhesive layer is already adhering to the patient's skin. As a result, the handling is further simplified. It is also possible for a part of the cover to be free from the adhesive layer that is intended to form a tab, with which the cover layer, for example the film or the paper, can easily be pulled off from the carrier material.

The section of the cover not provided with the adhesive layer also permits the cover to be pulled off easily from the patient's skin subsequently, since the section free from the adhesive layer forms a tab which can easily be gripped with the fingers.

The adhesive layer at the underside of the sensor may be applied directly or indirectly (transfer print) with suitable coating or printing methods. The adhesive should be skin-compatible and biocompatible. It may, for example, consist of a copolymerisate (e.g., acrylate) and be water-soluble. Instead of an acrylate adhesive, however, other adhesives known to the person skilled in the art may also be used. The adhesive force of the sensor may be adjusted by the quantity of the applied adhesive. The layer thickness of the adhesive layer depends on the adhesive used, the nonwoven fabric used, and the desired adhesive force and should preferably be determined individually for each material pairing. The adhesive should preferably be selected and the adhesive force adjusted in such a way that the cover can be detached again relatively painlessly. As a result of the large adhesive area of the sensor, a secure hold of the cover may be guaranteed even with a relatively small adhesive force.

The adhesive layer present at the underside of the cover is preferably an adhesive layer impermeable to liquid, but which is preferably permeable to vapor. A material permeable to liquid, in particular a nonwoven fabric, may thus be used for the carrier material.

The device according to the present invention for detecting moisture is preferably made available individually and packaged in a sterile manner. An ethylene oxide sterilization (EO) as well as all kinds of radiation sterilization can be considered as sterilization processes. γ-sterilization is preferred.

The device according to the present invention for monitoring an access to a patient, in particular for monitoring the vascular access in an extracorporeal blood treatment, comprises, apart from the device according to the present invention for detecting moisture, an evaluation unit to which the moisture sensor of the device for detecting moisture can be connected. The transmission of data between the device for detecting moisture and the evaluation unit of the monitoring device preferably takes place via a connection cable. The connection cable preferably comprises a connection part with spring-loaded contacts, which can be connected to the contact elements of the moisture sensor of the device for detecting moisture.

The evaluation unit comprises a unit for determining the resistance and/or the capacitance of the moisture sensor of the device for detecting moisture. The evaluation unit is preferably designed in such a way that both resistive moisture sensors, which change their resistance as a function of moisture, as well as capacitive moisture sensors, which change their capacitance as a function of moisture, can be evaluated.

For the resistive measurement, it is known to apply a direct or alternating voltage to the resistive moisture sensor, which leads to a current flow in the sensor as a function of the moisture present at the sensor. In order to be able to take measurements with both a resistive and a capacitive moisture sensor, direct voltage pulses, preferably of approx. 25 μs duration, with a pulse duty factor preferably ≦50%, are preferably applied to the moisture sensor as a measurement signal. The measurement signal makes a direct voltage available for the resistive sensor for the duration of approx. 25 μs, but also an alternating voltage for the capacitive sensor in a frequency of approx. 40 KHz. A further advantage of the measurement with short direct voltage pulses is that the direct voltage pulses do not represent a hazard to the patient.

For the resistive and/or capacitive measurement, the rectangular signal is preferably applied to the moisture sensor by means of a resistive and/or capacitive voltage divider. If the resistance and/or capacitance of the moisture sensor changes as a function of the moisture, the voltage divider ratio also changes and, with the latter, the resistance to be ascertained and/or the capacitance to be ascertained. For the evaluation of a resistive moisture sensor, the voltage at the voltage divider is measured only during the direct voltage pulse.

Since the connection cable between the moisture sensor and the evaluation unit also has a capacitive component apart from the resistive component, it is possible to check by means of a suitable measurement whether an electrical connection is produced with the connection cable between the moisture sensor and the evaluation unit of the monitoring device, i.e. that the connection cable is correctly connected to the device for detecting moisture and the monitoring device.

In a particularly preferred embodiment of the monitoring device, the measurement results are transmitted from the evaluation unit wirelessly to the device with which fluid is fed to the patient and/or carried away from the patient via a hose line, in particular to the extracorporeal blood treatment apparatus. For this purpose, the monitoring device comprises a transmitting unit and a receiving unit as spatially separated units. The receiving unit is preferably a component of the extracorporeal blood treatment apparatus. It is, however, also possible to connect the evaluation unit to the control unit of the extracorporeal blood treatment apparatus via a further connection cable. A bi-directional data transfer is possible when two transmitting and/or receiving units are provided as spatially separated units. For example, a transmitting and/or receiving unit of the monitoring device can communicate with a transmitting and/or receiving unit which is provided in the blood treatment apparatus.

The receiving unit or transmitting and/or receiving unit is preferably a part of the central control unit of the extracorporeal blood treatment apparatus or is connected to the control unit, so that in the event of blood issuing at the puncture point, the control unit can perform suitable interventions in the machine control, for example it can interrupt the blood flow and emit an alarm.

The monitoring device preferably cooperates with the control unit of the blood treatment apparatus in such a way that the blood treatment apparatus is transferred into a safe state for the patient in the event of a malfunction. For this purpose, the control unit may stop the blood pump disposed in the extracorporeal blood circuit and/or close the arterial and/or venous hose clamp in the extracorporeal blood circuit. The control unit may also emit an acoustic and/or optical alarm.

For the wireless transmission of the measurement results, the known radio modules with frequencies of, for example, 2.4 GHz as well as suitable communication logs are available to the person skilled in the art. The measurement results may be transmitted at cyclical intervals to the dialysis machine.

For the connection of the connection cable to the contact elements of the moisture sensor, the connection cable comprises a connection part with spring-loaded contacts, which can be connected electrically to the contact elements of the moisture sensor. It is possible to provide one or more contact pairs on the moisture sensor, so that the plug can easily be connected to the moisture sensor on different sides. For example, it is possible to provide a contact pair at right angles to the longitudinal direction of the cover and a contact pair in the longitudinal direction of the cover. The handling is thus further facilitated.

The power supply of the evaluation unit of the monitoring device preferably takes place with a battery, e.g., a storage battery. The evaluation unit may be switched on by the user, as a result of which an assignment between evaluation unit and dialysis machine may take place automatically. For this purpose, the monitoring device preferably comprises a pushbutton or switch. The evaluation unit preferably cannot be switched off again by the user with the pushbutton or switch, so that it is ensured that the monitoring device is always active. It should only be possible to switch off the monitoring device via the dialysis machine, when it is ensured that the treatment is to be interrupted or has ended. A corresponding signal for switching off the monitoring device may be transmitted from the dialysis machine, for example by radio, to the evaluation unit of the monitoring device.

In order to ensure the longest possible operation of the monitoring device, the current consumption should preferably be kept as low as possible. This may be achieved by the fact that the transmitting and receiving unit of the monitoring device is active only during the data transfer. The evaluation unit should also only be active when the measurement results are being read out from the moisture sensor. After acquisition and evaluation of the measurement results, the monitoring device is preferably put into a low-power/sleeping mode. The current consumption may be reduced by these measures and the operating period of the monitoring device may thus be extended considerably without having to replace the battery or recharge the storage battery.

The device according to the present invention for monitoring an access to a patient can form a separate unit or also be a component of the device with which fluid is fed to the patient and/or withdrawn from the patient, in particular a component of the extracorporeal blood treatment apparatus. If the monitoring device according to the present invention is a component of the blood treatment apparatus, the monitoring device according to the present invention may make use of specific subassemblies or components which are in any case present in the blood treatment apparatus.

In principle, other embodiment are also conceivable, e.g., wherein the pad covers the puncture point completely and even comprises a plurality of cutouts, e.g., a plurality of openings, with the purpose of allowing the fluid to be detected to penetrate through the openings onto the outer surface of the pad and to wet the strip conductors there. It would, however, also be conceivable for the pad not to comprise any cutout at all and to cover the puncture point completely. In such embodiments, however, the puncture point would be concealed and not visible.

Various examples of embodiment of the present invention are explained in greater detail below by reference to the drawings.

BRIEF DESCRIPTION OF THE DRAWINGS

FIG. 2 shows an example embodiment of the device for detecting moisture of the device for monitoring the arterial and venous vascular access in plan view.

FIG. 3 shows the device of FIG. 2 in a view from below.

FIG. 4 shows a cross-section through the device of FIG. 2.

FIG. 5 shows the device for detecting moisture of FIG. 2 lying on the patient's skin, together with the cannula.

DETAILED DESCRIPTION

Figure 1:
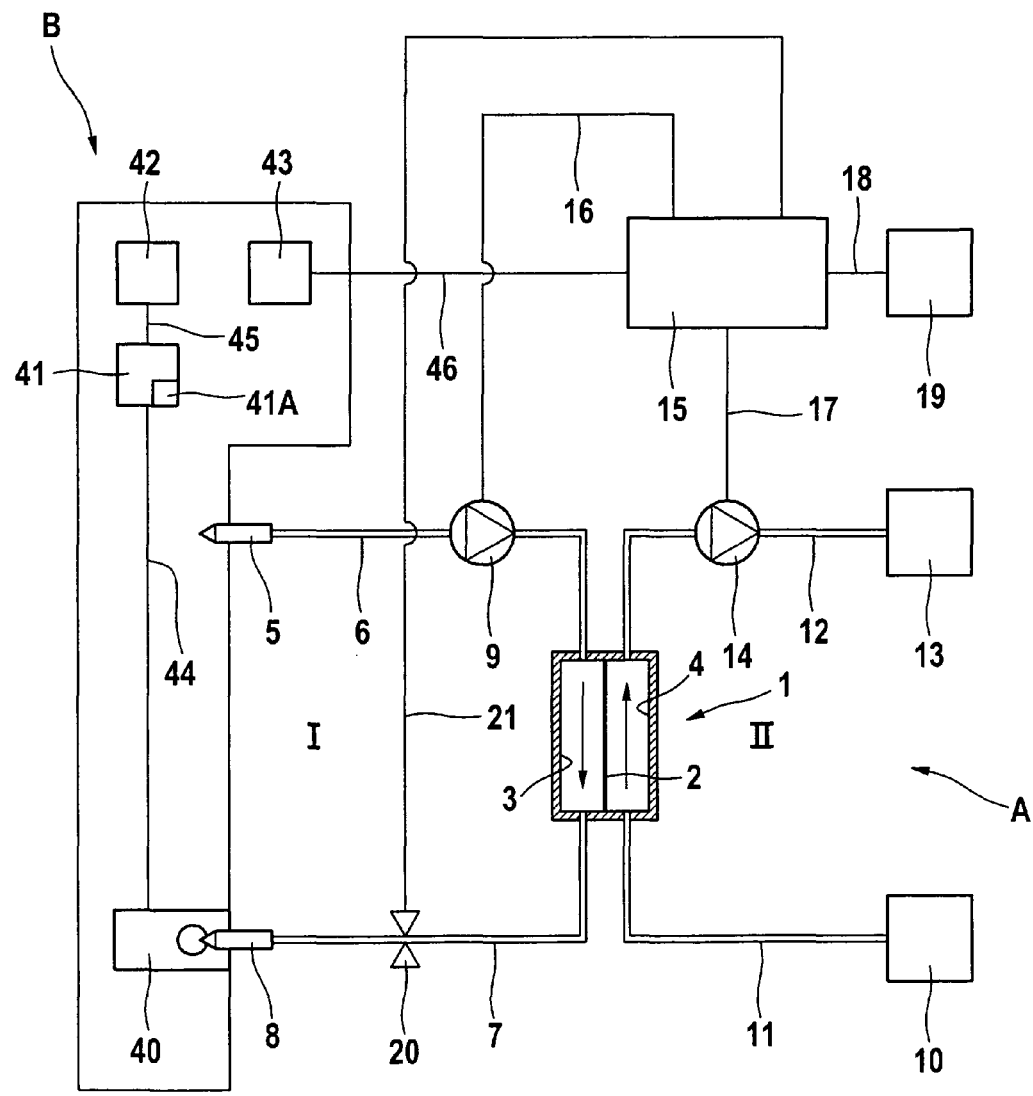
FIG. 1 shows the main components of a hemodialysis apparatus, which comprises a device for monitoring the arterial and venous vascular access.

FIG. 1 shows the main components of a hemodialysis apparatus (A), which comprises a device (B) for monitoring the venous and arterial vascular access. In the present example embodiment, the monitoring device (B) is a component of the hemodialysis apparatus (A). The hemodialysis apparatus will first be described by reference to FIG. 1.

The hemodialysis apparatus comprises a dialyzer 1, which is divided by a semipermeable membrane 2 into a blood chamber 3 and a dialyzing fluid chamber 4. An arterial hose line 6 is connected by means of an arterial puncture cannula 5 to one of the patient's arteries, said arterial hose line leading to the inlet of chamber 3 of the dialyzer. Leading away from the outlet of chamber 3 of the dialyzer is a venous hose line 7, which is connected by means of a venous puncture cannula 8 to one of the patient's veins. Arterial hose line 6 is inserted into an occluding blood pump 9, which conveys the blood in extracorporeal blood circuit I. Dialyzing fluid circuit II of the hemodialysis apparatus comprises a dialyzing fluid source 10, to which a dialyzing fluid supply line 11 is connected, which leads to the inlet of dialyzing fluid chamber 4 of the dialyzer. Departing from the outlet of dialyzing fluid chamber 4 of dialyzer 1 is a dialyzing fluid discharge line 12, which leads to a drain 13. A dialyzing fluid pump 14 is incorporated into dialyzing fluid discharge line 12.

The control of the dialysis apparatus is assumed by a central control unit 15, which controls blood pump and dialyzing fluid pump 9, 14 via control lines 16, 17. Central control unit 15 is connected via a data line 18 to an alarm unit 19, which emits an optical and/or acoustic alarm in the event of a malfunction.

Located downstream of blood chamber 3 of dialyzer 1 on venous hose line 7 is an electro-magnetically actuated venous hose clamp 20, which is closed via a further control line 21 by central control unit 15 if the venous puncture cannula (needle) should slip out of the vascular access. Moreover, control unit 15 stops pump 9 after the slipping-out of the cannula.

In the present example embodiment, monitoring device (B) is used to monitor the venous vascular access. Monitoring device (B) comprises a device 40 for detecting moisture, which is disposed at the puncture point. This detection device 40 is represented only schematically in FIG. 1. The monitoring device also comprises an evaluation unit 41, a transmitting unit 42 and a receiving unit 43. In place of a transmitting unit 42 and a receiving unit 43, however, two transmitting/receiving units communicating with one another may also be provided for a bi-directional data transfer. One of the transmitting/receiving units may also be assigned to the dialysis machine. Evaluation unit 41 of monitoring unit B is connected electrically to detection device 40 by means of a connection line 44. Evaluation unit 41 is connected via a data line 45 to transmitting unit 42, whilst receiving unit 43 of monitoring device B is connected via a data line 46 to central control unit 15 of the dialysis apparatus.

Whereas evaluation unit 41 and transmitting unit 42 together with detection device 40 are assigned to the patient, receiving unit 43 is assigned to the dialysis apparatus. In the event of blood issuing at the puncture point, evaluation unit 41 generates a control signal, which transmitting unit 42 transmits and receiving unit 43 receives. The control signal is transmitted via data line 46 to central control unit 15, which performs an intervention into the blood treatment. Central control unit 15 generates an alarm signal, so that alarm unit 19 emits an acoustic and/or optical alarm. In addition, control unit 15 stops blood pump 9 and closes hose clamp 20.

A first example embodiment of device 40 for detecting moisture, which is to be placed on the patient's skin at the puncture point, is described below by reference to FIGS. 2 to 5. FIG. 2 shows detection device 40 in plan view, whilst FIG. 3 shows the device in a view from below. FIG. 4 shows a cross-section through the device. FIG. 5 shows the device lying on the patient's skin in plan view together with the cannula.

The detection device is constituted as a cover 22 made of a flexible material which is to be placed on the patient's skin. Cover 22 comprises an upper side 22A facing away from the patient's skin (FIG. 2) and an underside 22B to be placed on the patient's skin (FIG. 3). The cover is a rectangular pad with rounded-off corners, which has two longitudinal sides 22C and two narrow sides 22D. Located in the center of the pad between longitudinal and narrow sides 22C, 22D is a circular cutout 23. A predetermined rupture line 24 in the form of a perforation extends from circular cutout 23 to one of the two longitudinal sides 22C of the pad. Pad 22 may be divided conceptually into a first wide section 26 and a second narrow section 27. Located in pad 22 is a moisture sensor 28 for detecting moisture at the puncture point. Pad 22 comprises a plurality of layers which will be described below.

Pad 22 comprises a biocompatible, skin-compatible, soft carrier material 29 made of a flexible nonwoven fabric, for example of a cellulose fiber/polyester fiber mixture with a layer thickness of, e.g., approx. 150 μm. On account of its open structure, the nonwoven fabric is both air permeable and water-vapor permeable. Moisture sensor 28 is located on the upper side of carrier material 29. Sensor 28 comprises two strip conductors 28A, 28B, whereof one strip conductor 28A leads to a terminating resistor 28C and second strip conductor 28B leads away from the terminating resistor. The ends of the two strip conductors are connected to electrical contact elements 28D and 28E. Strip conductors 28A, 28B form a conductor loop around circular cutout 23. The conductor loop lies in broad section 26 of the pad, whilst contact elements 28D, 28E lie in narrow section 27 of the pad.

Both contact elements 28D and 28E for making contact with moisture sensor 28 lie in narrow section 27 of pad 22 beside one another in a direction at right angles to the longitudinal direction of the pad. Located in narrow section 27 are two further contact elements 28F and 28G, which are connected electrically by further strip conductors 28H and 28I to the other contact elements 28D and 28E. These contact elements 28F and 28G are disposed beside one another in the longitudinal direction on the pad. The two pairs of contact elements enable the connection of the moisture sensor to evaluation unit 23 via connection cable 26 with a suitable connection part, which will be described in more detail below. Since two pairs of contact elements are available, the plug can be connected either to the one or other pair of contact elements. It is therefore possible to connect the plug to the pad either at the narrow side or longitudinal side.

Strip conductors 28A, 28B and 28H, 28I are printed in the screen-printing process on the upper side of carrier material 29. Contacts 28D and 28E as well as 28F and 28G are also printed on the upper side of the carrier material. Terminating resistor 28C is also a printed resistor, which is printed on the upper side of the carrier material. Apart from the strip conductors and contact elements, further markings 30 or suchlike can also be printed on the upper side of carrier material 29 which give the user instructions for the handling of the pad, for example for the connection of the plug to the pad.

A moisture-permeable cover layer 31 is preferably located on the upper side of carrier material 29, i.e. on the strip conductors and contact elements. False alarms due to inadvertent contact with the strip conductors and contact elements can thus be avoided. Cover layer 31 also facilitates the cleaning of the pad if it comes into contact with fluids.

At the underside, carrier material 29 is provided with an adhesive layer 32 impermeable to fluid, but permeable to vapor. Adhesive layer 32, however, extends only over broad section 26 with the circular cutout, but not over narrow section 27 on which contact elements 28E, 28D and 28F, 28G are disposed. Since narrow section 27 with the contact elements does not adhere to the patient's skin, the connection part for the connection of moisture sensor 28 can easily be connected to the pad. For this purpose, narrow section 27 can be lifted with the fingers. Narrow section 27 also forms a tab for subsequent pulling-off of the pad from the patient's skin. Adhesive layer 32 and the section of the underside of carrier material 29 free from the adhesive layer covered with a silicone paper 33 which is biocompatible and skin-compatible. It should be able to be easily detached from adhesive layer 32, but without detaching the adhesive layer itself from carrier material 29. Since silicone paper 33 does not adhere to narrow section 27 of carrier material 29 on account of the absence of the adhesive layer, silicone paper 33 can easily be pulled off before the placing of the pad on the patient's skin. In order to facilitate the pulling-off of silicone paper 33 even with rubber gloves, other sections can also be left free from the adhesive layer, for example at the longitudinal sides of the sensor, so that the silicone paper can be pulled off from two sides. Further tabs can also be formed on silicone paper 33 with which the paper can be gripped. These tabs can also be located on carrier material 29.

Figure 6:
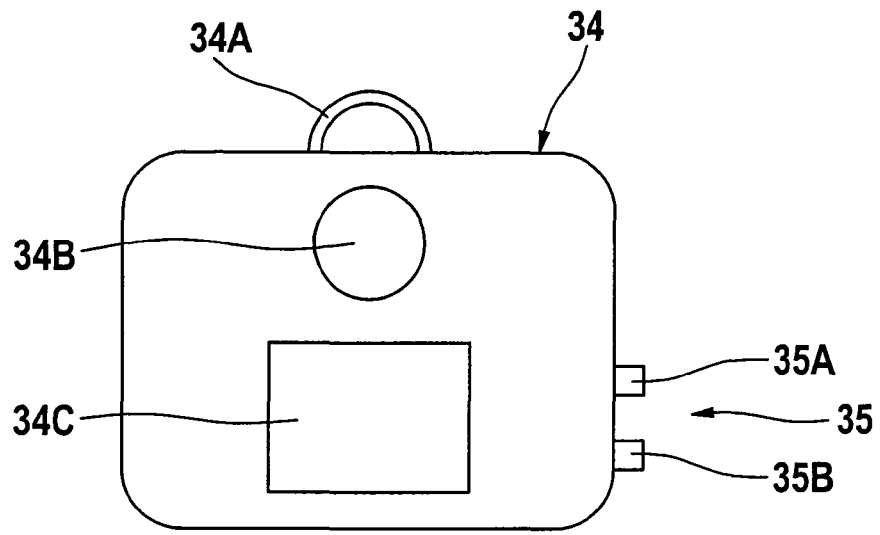
FIG. 6 shows the housing of the device for monitoring the arterial and venous access.
Figures 7A, 7B:
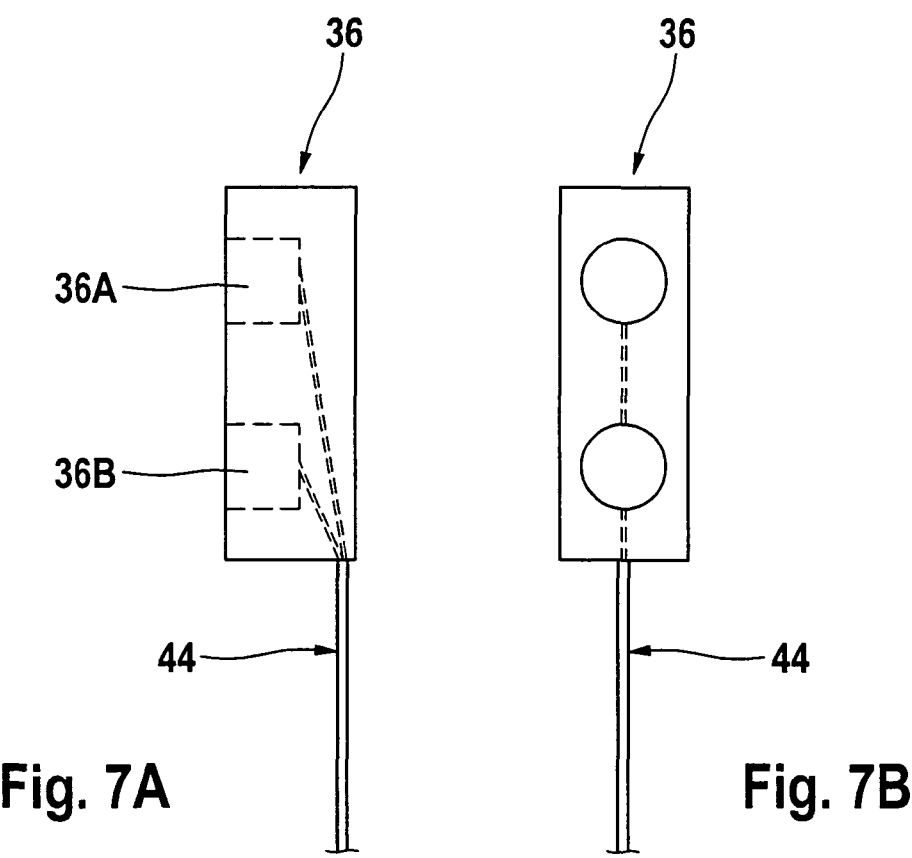
FIGS. 7A and 7B show the plug unit of the connection cable for connecting the device according to the present invention for detecting moisture.

FIG. 6 shows in a schematic representation housing 34, which is to be fitted on the patient side and which accommodates evaluation unit 41 and transmitting and receiving unit 42 of monitoring device B according to the present invention. At the upper side, housing 34 comprises a strap 34A, in which a clip (not illustrated) may be suspended which is provided in close proximity to the patient, for example on the bed or on the patient's clothing. The clip (not illustrated) is not a component of monitoring device B. The clip, which is to be fixed detachably to strap 34A of housing 34, can thus readily be discarded in the event of damage or soiling. Located on housing 34 is a pushbutton 34B for switching on evaluation unit 41 and transmitting and receiving unit 42. The device cannot however be switched off with pushbutton 34B. Furthermore, a closable battery compartment 34C is provided for inserting the battery for the power supply. Located at the side of housing 34 is a plug unit 35 for connecting detection device 40 to evaluation unit 41 of monitoring device B. Whereas plug unit 35 on housing 34 comprises two plugs 35A, 35B disposed beside one another, connection line 44 comprises at one end a corresponding socket unit 36 with two sockets 36A, 36B disposed lying beside one another at an identical distance (FIGS. 7A and 7B). Plugs 35A, 35B and sockets 36A, 36B of plug unit and socket unit 35, 36 are constituted in the manner of pushbuttons which can easily be connected to one another and easily detached from one another. The pushbutton contacts are enclosed in plug unit and socket unit 35, 36, so that the contacts are for the most part resistant to cleaning agents and disinfectants as well as other contaminants after the connection of plug and socket. Plug unit and socket unit 35, 36 permits a durable connection which can easily be detached.

Figure 8B:
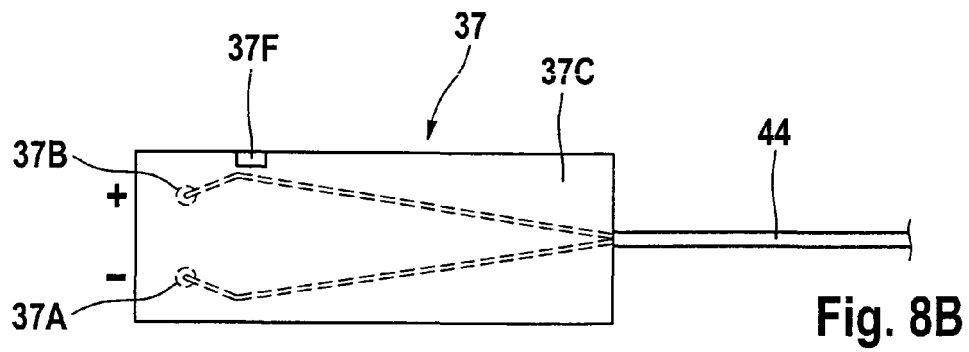
FIGS. 8A and 8B show a first example embodiment of the connection part of the connection cable.
Figure 8A:
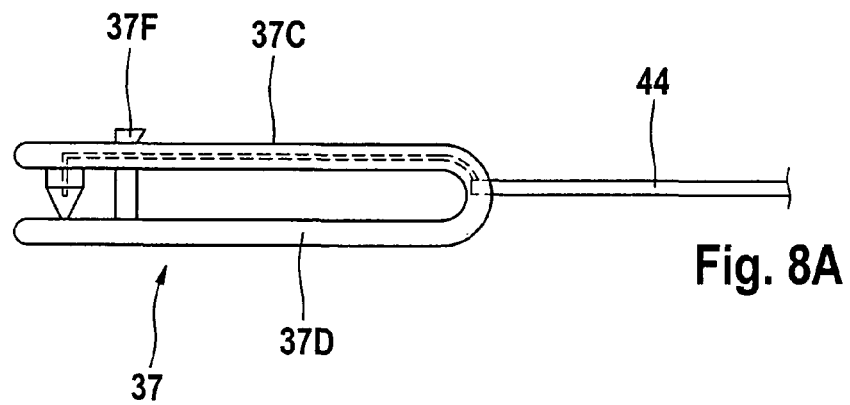

A connection part 37 is present at the other end of connection cable 44 for the connection of connection cable 44 to moisture sensor 28. FIGS. 8A and 8B show a simplified schematic representation of a first embodiment of connection part 37 in side view and plan view. The connection cable can be connected with this connection part 37 to contact elements 28D, 28E, which are disposed at narrow side 22D of pad 22. Connection part 37 comprises two pin-shaped contacts 37A, 37B, which are disposed with an identical spacing to contact elements 28D, 28E. Connection part 37 is constituted in the manner of a clamp which comprises an upper and lower spring-loaded bracket 37C, 37D. It is preferably a one-piece plastic part, the upper and lower brackets (arms) 37C, 37D being able to be connected to one another in a spring-loaded manner, for example by means of a film hinge or suchlike.

Upper bracket 37C is held by a locking element 37F, which engages at the upper side of upper bracket 37C and is fixed to lower bracket 37D, in a position in which pin-shaped contacts 37A, 37B on upper bracket 307C are pressed against lower bracket 37C, against the spring tension of the two brackets 37C, 37D. After the release of locking element 37F, upper bracket 37C springs up, so that connection part 37 can be connected to pad 22.

In order to be able to produce an electrical connection between contacts 37A, 37B of connection part 37 and contact elements 38D, 38E of the pad, connection part 37 is pushed laterally onto the pad with the brackets opened. The two brackets 37C, 37D are then pressed together with two fingers until locking element 37F locks home. Pin-shaped contact elements 37A, 37B of connection part 37 engage in the relatively soft nonwoven fabric of the pad, as a result of which connection part 37 is held securely to the pad. In order that contacts 28E, 28D of pad 22 can meet better, it is possible to provide on the pad markings or suchlike which like the contact elements are printed on the carrier material.

Figure 9B:
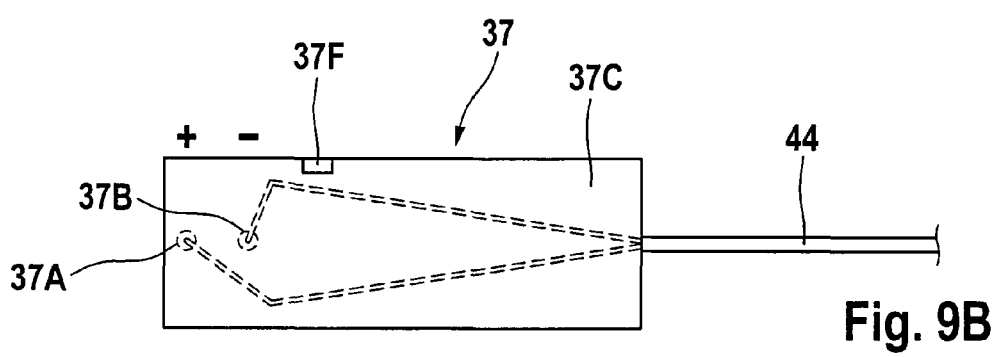
FIGS. 9A and 9B show a second example embodiment of the connection part of the connection cable.
Figure 9A:
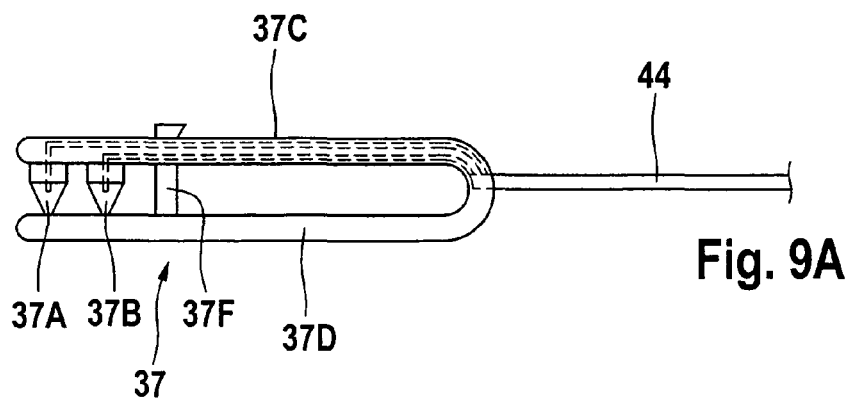

FIGS. 9A and 9B show an alternative embodiment of connection part 37, which differs from the connection part described by reference to FIGS. 8A and 8B solely in that the two contacts 37A, 37B are disposed not beside one another, but one behind the other. The parts of connection part 37 corresponding to one another are therefore also provided with the same reference numbers. Connection part 37 of FIGS. 9A and 9B is intended for the connection to the two contact elements 28G, 28F, which are disposed at longitudinal side 22C of pad 22. It is however also possible to connect the connection part of FIGS. 8A and 8B to contact elements 28F, 28G at longitudinal side 22C and the connection part of FIGS. 9A and 9B to contact elements 28D, 28E at the narrow side of pad 22. A connection to different sides of the pad is thus possible, the respective connection part being placed on the pad either at the longitudinal side or narrow side and then pointing in different directions.

Monitoring device B described by reference to FIGS. 2 to 4 is handled as follows in combination with extracorporeal blood treatment apparatus A.

FIG. 5 shows the device for detecting moisture lying on the patient's skin together with the cannula comprising a puncture wing. In the case where arterial or venous cannula 5, 8 is already connected, pad 22 is torn at weakening line 24 (perforation), so that a slit arises. Pad 22 is then pushed over the cannula which is already put in place. Puncture wing 5A, 5B provided on cannula 5, 8 can then be fixed, the puncture point lying within circular cutout 23 of pad 22. If blood issues at the puncture point, the blood cannot penetrate into pad 22 at the underside impermeable to liquid. The blood can however flow through circular cutout 23 and get onto the upper side of pad 22, at which the pad is permeable to liquid. The blood seeps into nonwoven fabric 29 and arrives at moisture sensor 28, the resistance or capacitance of which changes. Evaluation unit 41 measures the resistance or the capacitance of moisture sensor 28 and compares the resistance or the capacitance with a preset limiting value. If the limiting value is exceeded, evaluation unit 41 generates a control or alarm signal, which transmitting and receiving unit 42 on the patient side transmits to transmitting and receiving unit 43 on the dialysis machine side. Receiving unit 43 then generates a control signal which is received by central control unit 15 of the dialysis machine. Control unit 15 then interrupts the blood flow through venous hose line 7 by closing electrically actuated hose clamp 20, and alarm unit 19 emits an acoustic and/or optical alarm.

In the case where cannula 5 or 8 has not yet been put in place, pad 22 does not need to be severed at weakening line 24 (perforation). In this case, the puncture of the skin site can take place through circular cutout 23 of the pad after pad 22 has been placed on the patient's skin.

Terminating resistor 28C of moisture sensor 28 permits both the monitoring of the integrity of the two strip conductors of moisture sensor 28 as well as the correct connection of connection cable 44. For this purpose, evaluation unit 41 of monitoring device B comprises a unit which checks whether the resistance of the moisture sensor lies above or below a limiting value in the presence of a predetermined air humidity. If the resistance between the contact elements of the moisture sensor diverges sharply from the terminating resistor, for example is much greater than the terminating resistor, the conclusion is drawn that a strip conductor is damaged or interrupted or the connection cable is not correctly connected. If this is the case, the evaluation unit prompts the user, by an optical and/or acoustic signal, to check the moisture sensor and the connection of the connection line.

Figure 10A:
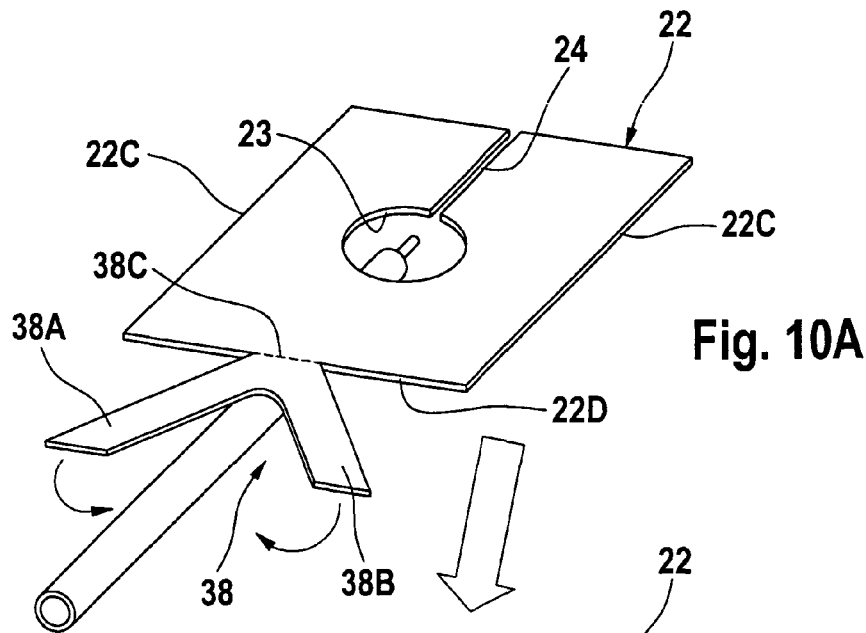
FIGS. 10A to 10C show further examples of embodiment of the device according to the present invention for detecting moisture together with a puncture cannula.
Figure 10B:
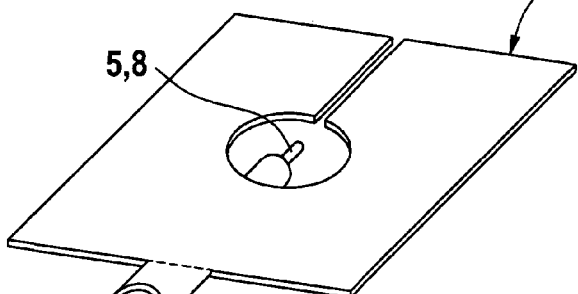

FIGS. 10A and 10B show a further embodiment of pad 22 according to the present invention together with cannula 5, 8, the same reference numbers again being used for parts corresponding to one another.

The pad of FIGS. 10A and 10B again comprises a circular cutout 23 and a weakening line 24. The pad of FIGS. 10A and 10B differs from the previously described embodiments in that a securing device 38 for fixing cannula 5, 8 is formed at narrow side 22D, with which hose line 6, 7 leading to cannula 5, 8 can be fixed. Securing device 38 is a V-shaped strip which is provided at the underside with an adhesive layer (plaster). V-shaped plaster 38 is formed with the front part on narrow side 22D of pad 22, at which the two legs 38A, 38B of the V-shaped plaster meet. Connection point 38C between plaster 38 and pad 22 is provided with a weakening line 38C (perforation), which runs parallel to narrow side 22D of pad 22. V-shaped plaster 38 can however also be formed on longitudinal side 22C of the pad.

FIG. 10A shows pad 22 for the fixing of cannula 6, 7. For the fixing of cannula 6, 7, the two legs 38A, 38B of plaster 38 are wrapped firmly around hose line 6, 7 leading to the cannula (FIG. 10B), so that the hose line of the cannula is fixed to pad 22. If the hose line is subjected to tensile load, perforation 38C tears, so that pad 22 remains at the puncture point.

Figure 10C:
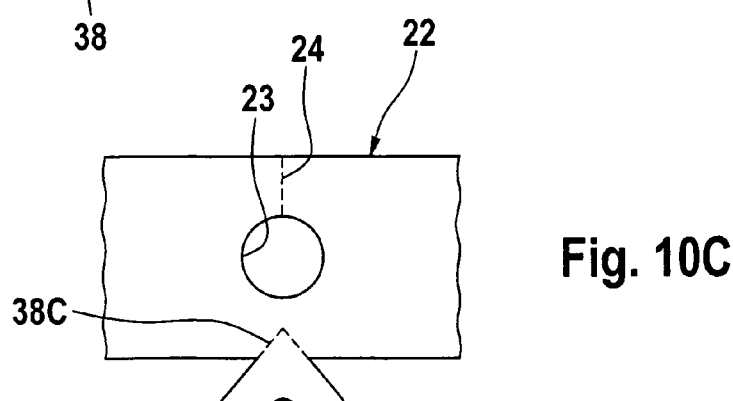

FIG. 10C shows an alternative embodiment of pad 22, which differs from the embodiment of FIGS. 10A and 10B in that weakening line 38C does not run in a straight line, but is formed V-shaped. Depending on the length and shape of the perforation or the size of the area of the connection point between plaster and pad, it is possible to set different tensile forces with which the fixing of the hose can be detached. Weakening line 38 should be formed in such a way that, in the presence of a tensile load in the longitudinal direction of the hose line, a relatively high tensile force is required to tear plaster and pad apart, whereas both parts can easily be separated from one another in the presence of a tensile load at right angles to the longitudinal direction. It is thus possible, after the blood treatment, to separate plaster 38 together with hose line 6, 7 and cannula 5, 8 easily from pad 22.

Figure 11:
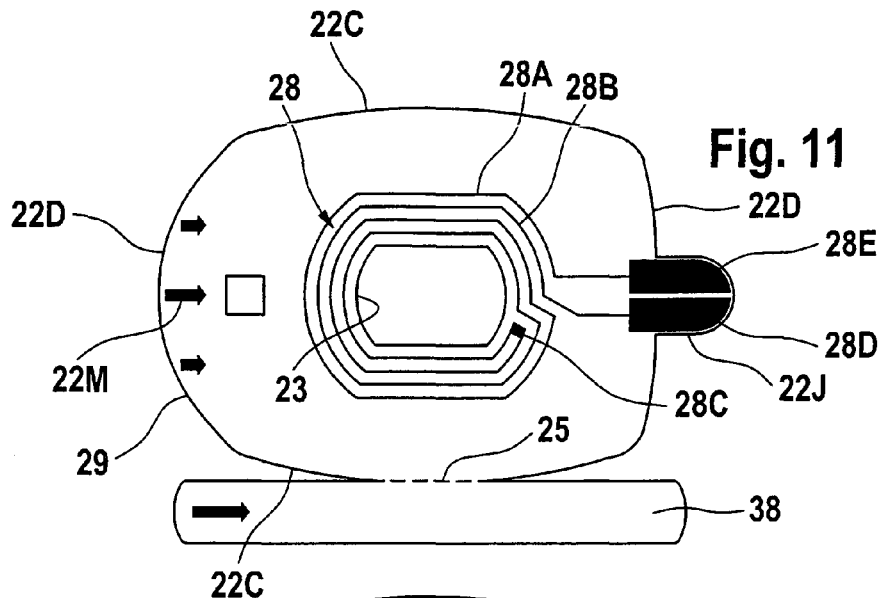
FIG. 11 shows a further example embodiment of the device for detecting moisture in plan view.
Figure 12:
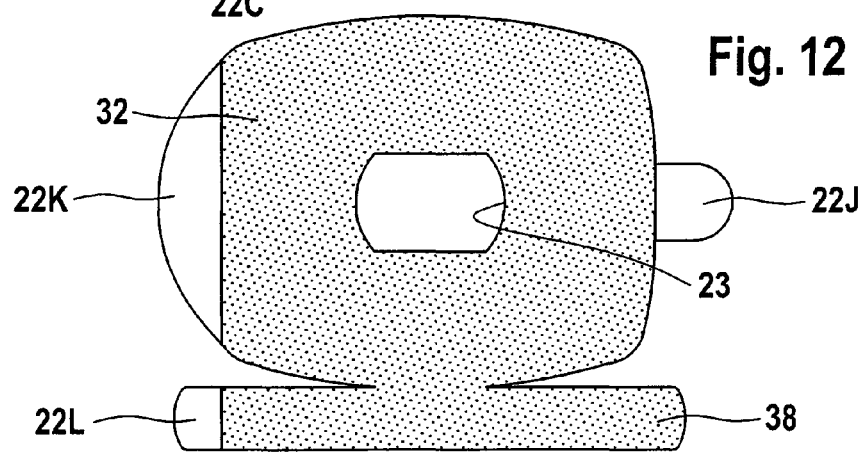
FIG. 12 shows the device of FIG. 11 in a view from below.
Figure 13:
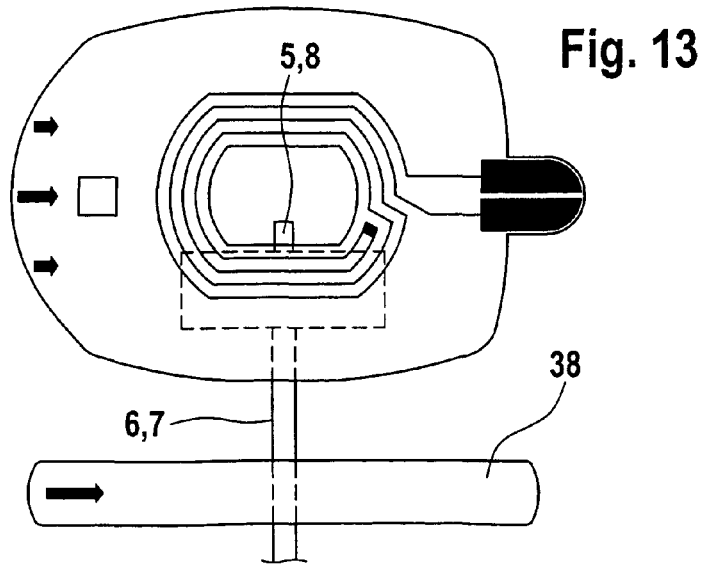
FIG. 13 shows the device for detecting moisture of FIG. 12 together with the cannula.

FIGS. 11 to 13 show a further embodiment of pad 22, which differs from pad 22 described by reference to FIGS. 2 to 5 in terms of the shape, but has the same layer structure. The same reference numbers are therefore also used for parts corresponding to one another.

The pad has an essentially oval shape with longitudinal and narrow sides 22C, 22D, a securing device 38 for the cannula and its hose line being formed at one of longitudinal sides 22C. The securing device is a narrow plaster strip 38 which is connected at the longitudinal side via a perforation line 25, so that the strip can easily be separated from pad 22.

Moisture sensor 28 and cutout 23 are located in the center of the oval section of pad 22. The pad thus has a symmetrical structure, so that it can be fixed together with arterial or venous cannula 5, 8 both on the left arm and right arm of the patient. The pad does not comprise a perforation in the region of cutout 23, since the pad is intended to be placed on the patient's skin only after cannula 5, 8 has been put in place. The pad, which is to be handled like a plaster, is used not only for the detection of blood, but also in practical terms for the fixing of the cannula.

Pad 22 again comprises a carrier material 29, in particular a nonwoven fabric, which is provided at its underside with an adhesive layer 32 impermeable to liquid, but permeable to vapor. At the upper side, the carrier material is provided with a first and second strip conductor 28A, 28B, one of the ends whereof is connected to a terminating resistor 28C and the other of the ends whereof is connected to contact elements 28D, 28E. Strip conductors 28A, 28B surround cutout 23 as a closed conductor loop, since a perforation is not present. Adhesive layer 32 is again covered with a silicone paper (not illustrated in the figures) which is pulled off before the pad is used.

Contact elements 28D, 28E lying beside one another are located on a tab 22J, which is formed at one of narrow sides 22D. Contact elements 28D, 28E on tab 22J are intended for a connection part 37 with pin-shaped contacts 37A, 37B, which is described by reference to FIGS. 9A and 9B.

Tab 22J for contact elements 28D, 28E is free from adhesive layer 32 at the rear side of carrier material 29. Corner regions 22K, 22L of pad 22 and of plaster strip 36 lying opposite tab 22J for contact elements 28D, 28E are also free from the adhesive layer, so that these regions form tabs with which they can easily be pulled off again from the patient's skin. Printed arrows 22M on sections 22K, 22L of pad 2 indicate the pulling direction.

The pad is handled as follows. Cannula 5, 8 is first put in place. Plaster strip 36 is then torn off from pad 22 and the silicone paper (not illustrated in the figures) is pulled off strip 36, so that adhesive layer 32 is exposed. Hose 6, 7 of cannula 5, 8 is then fixed to the patient's upper arm with plaster strip 36. After removal of the silicone paper, pad 22 is then stuck onto the patient's skin in such a way that tab 22J with contact elements 28D, 28E points to the outside of the arm. The effect of this is that connection cable 44 of connection part 37 to be connected to the pad cannot get entangled with arterial and venous hose line 6, 7. Since the pad is not completely covered with adhesive at the underside, the paper can easily be gripped with the tabs which are marked by arrows 22M. Connection part 37 with pin-shaped contacts 37A, 37B is now connected to contact elements 28D, 28E of tab 22J, so that the device can be put into operation.

Figure 14:
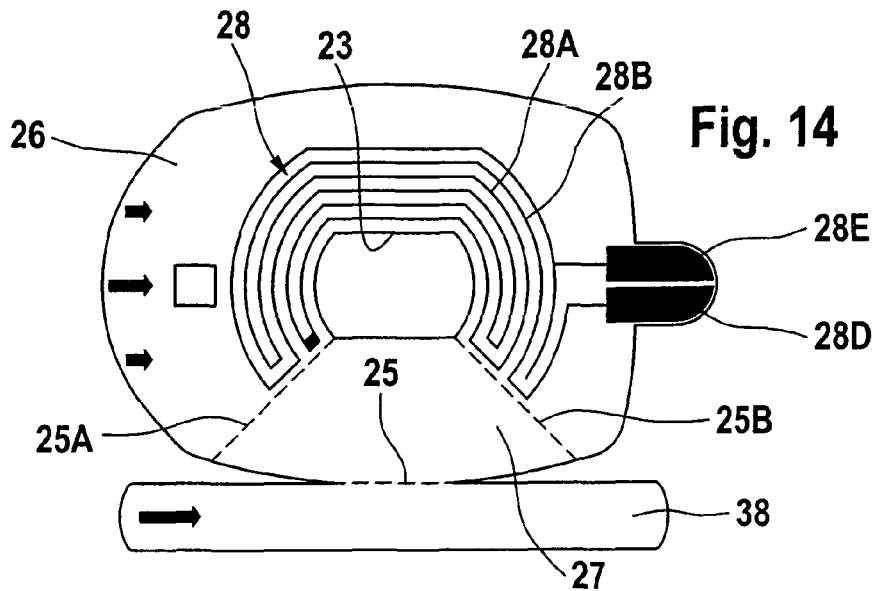
FIG. 14 shows a further example embodiment of the device for detecting moisture in plan view.
Figure 15:
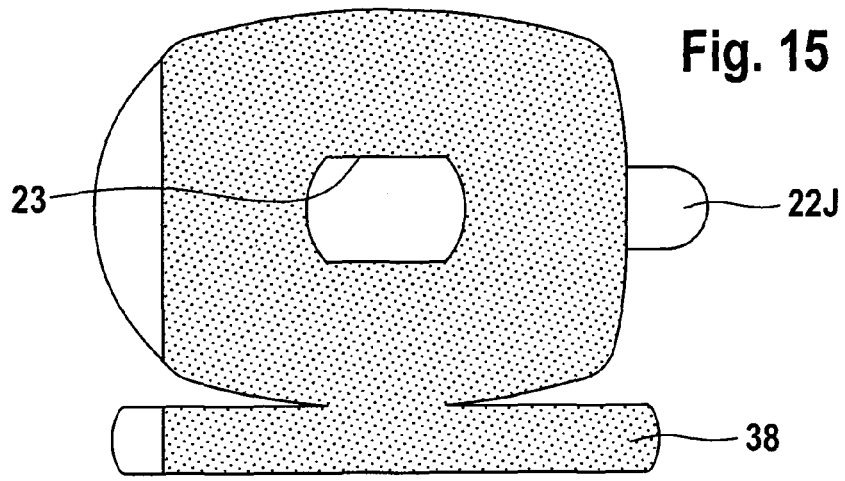
FIG. 15 shows the device of FIG. 14 in a view from below.
Figure 16:
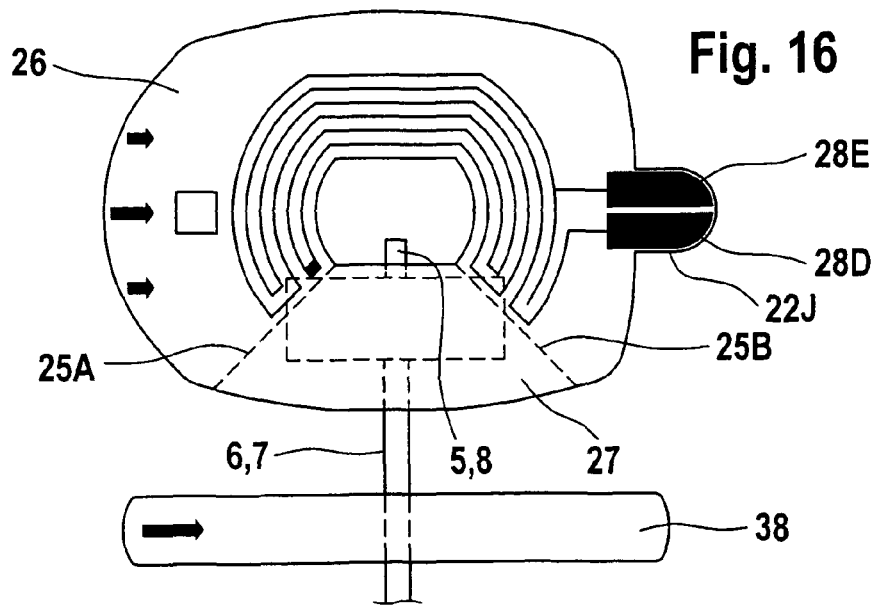
FIG. 16 shows the device for detecting moisture of FIG. 14 together with the cannula.

FIGS. 14 to 16 show an alternative embodiment of pad 22, which differs from pad 22 described by reference to FIGS. 11 to 13 solely in the design of moisture sensor 28 and the division of the pad into a first and second section 26 and 27. The parts corresponding to one another are therefore again denoted with the same reference numbers. Both sections 26 and 27 are separated from one another by the two predetermined rupture lines 25A, 25B running obliquely towards one another, which each extend on the edge of a longitudinal side 22C up to cutout 23 of pad 22. A first section 26 is thus created on which moisture sensor 28 is located, and a second essentially trapezoidal section 27, beneath which cannula 5, 8 and hose line 6, 7 extend when the pad is stuck onto the patient's skin (FIG. 16). The two strip conductor 28A, 28B of moisture sensor 28 extend up to predetermined rupture lines 25A, 25B, so that the conductor loop does not completely surround cutout 23.

The alternative embodiment of the pad of FIGS. 14 to 16 is handled like the embodiment of FIGS. 11 to 13. The pad is stuck onto the patient's skin after cannula 5, 8 has been put in place, the cannula and the hose line lying beneath the pad. The hose line is additionally fixed with plaster strip 36. The alternative embodiment has the advantage that, in the event of a tug on the cannula, the pad is not completely torn off from the patient's skin, but section 27 alone is separated from pad 22 to which the cannula is fixed, the two predetermined rupture lines 25A, 25B tearing up to cutout 23. Strip conductors 28A, 28B of moisture sensor 28 are not however severed. The device thus remains fully operational even after the needle has been torn away, so that the issuing of blood at the puncture point can be detected.

Figure 17A:
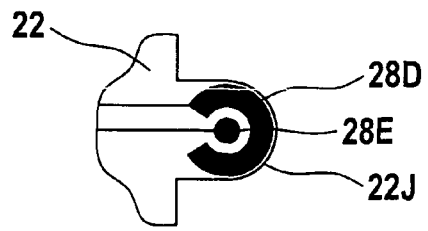
FIGS. 17A to 17C show the contact elements and the connection part of the device of FIG. 11 or FIG. 14 in different positions.
Figure 17B:
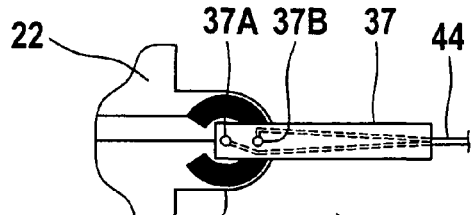
Figure 17C:
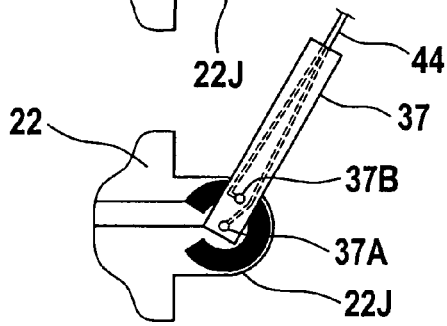

FIGS. 17A to 17C show an alternative embodiment of contact elements 28D, 28E, which may be provided on tab 22J of the pad of FIGS. 14 to 16 or of FIGS. 11 to 13. First contact element 28E is circular and disposed in the center of tab 22J, whilst second contact element 28D is formed circular-arc-shaped and surrounds first contact element 28E. Connected to contact elements 28D, 28E is connection part 37 with pin-shaped contacts 37A, 37B, said connection part being described by reference to FIGS. 9A and 9B. The advantage of the alternative embodiment of the contact elements lies in the fact that connection part 37 can be connected to pad 22 not only from a side, but also from different directions. FIGS. 17B and 17C show connection part 37 connected to the pad from two different directions. Connection cable 44 can thus run in the way that the given connection situation requires.

Figure 18:
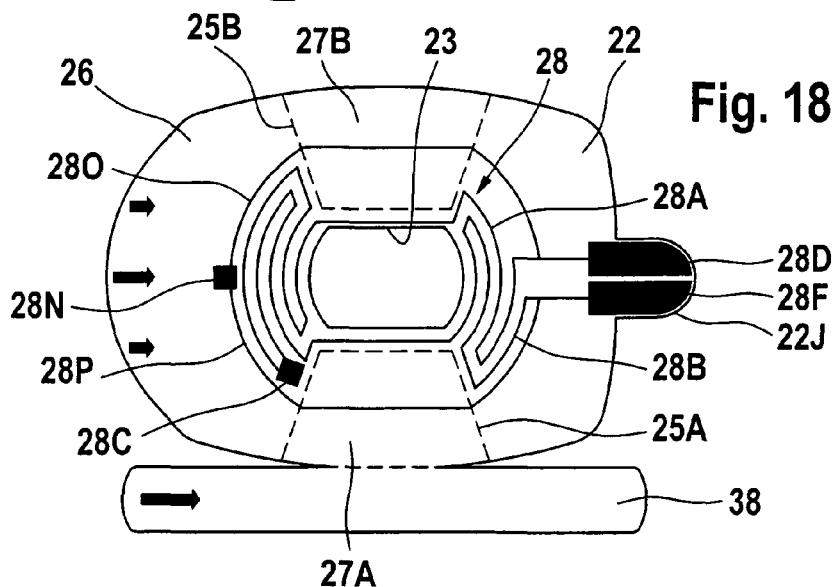
FIG. 18 shows a further example embodiment of the device for detecting moisture in plan view.
Figure 19:
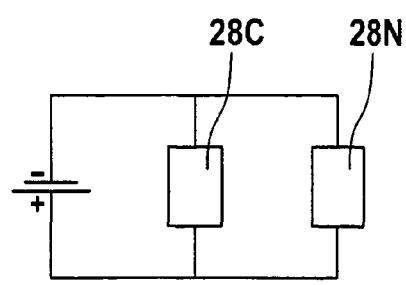
FIG. 19 shows an electrical equivalent circuit diagram of the device of FIG. 18.

FIGS. 18 and 19 show a further alternative embodiment of pad 22, which differs from pad 22 described by reference to FIGS. 14 to 16 in the design of moisture sensor 28. A further difference lies in the fact that not one separable section, but two separable, essentially trapezoidal sections 27A, 27B are provided, which are disposed symmetrically on both sides of cutout 23 of pad 22. The parts corresponding to one another are again denoted with the same reference numbers.

Separable sections 27A, 27B are separated by a first and second predetermined rupture line 25A, 25B from the other part of pad 22. Predetermined rupture lines 25A, 25B each comprise a section which runs from the edge of longitudinal side 22D of the pad up to the vicinity of cutout 23, a middle section running at a distance from cutout 23 and a third section running up to the edge of the longitudinal side of the pad. On account of the symmetrical structure, the pad can be fixed to the patient's left arm or right arm depending on the given connection situation. Cannula 5, 8 with hose line 6, 7 is passed beneath one of the two separable sections 27A, 27B.

Moisture sensor 28 comprises a first strip conductor 28A leading to a first terminating resistor 28C and a second strip conductor 28B leading away from the terminating resistor, the ends of the first and second strip conductor being connected electrically to contact elements 28E, 28D, which are applied on tab 22J. The two strip conductors 28A, 28B form a conductor loop, which surrounds cutout 23 of pad 22 and which does not extend over the two separable sections 27A, 27B of the pad.

A second terminating resistor 28N is connected in parallel with first terminating resistor 28C. FIG. 19 shows the electrical equivalent circuit diagram with the parallel connection of the two terminating resistors 28C, 28N. Leading away from first and second strip conductors 28A, 28B are a third and fourth strip conductor 28O, 28P, which lead to second terminating resistor 28N. Unlike first and second strip conductors 28A, 28B, third and fourth strip conductors 28O, 28P each run through one of the two separable sections 27A, 27B of pad 22.

If one of the two sections 27A, 27B is torn off in the event of a tug on the cannula or the hose line, first and second strip conductors 28A, 28B remain intact, since these strip conductors do not cross predetermined rupture lines 25A, 25B, but third and fourth strip conductors 28O and 28P are severed, since these strip conductors run through separated section 27A or 27B.

If, therefore, a section 27A or 27B is torn off, the resistance of the network changes. The network then only has a resistance which corresponds to first resistor 28C. Otherwise, the network has a resistance which is determined by the parallel connection of resistors 28C and 28N. In the event of bleeding, a resistance can be measured at contact elements 28E, 28D which diverges from the resistance which is determined by the parallel connection of resistors 28C and 28N. Evaluation unit 41 monitors the resistance between the contact elements and ascertains whether bleeding is present or the cannula together with respective section 27A, 27B of pad 22 has been torn away. It is concluded that there is bleeding if the resistance measured at the contact elements diverges by a predetermined amount from the resistance which results from the parallel connection of the two resistors. Even if the cannula with the section is torn off, the device remains operational. In this case, it is concluded that there is bleeding if the measured resistance diverges by a predetermined amount from first resistor 28C.

Figure 20:
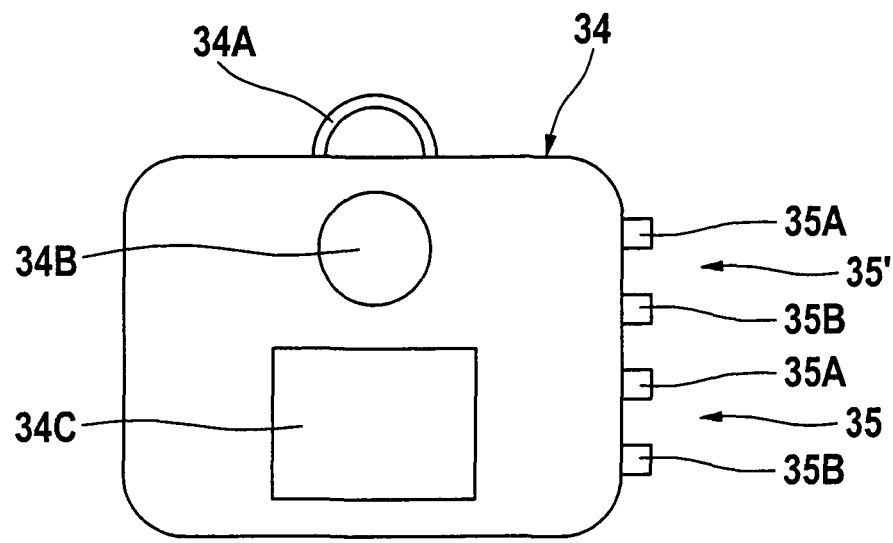
FIG. 20 shows a further example embodiment of the housing of the device for monitoring the arterial and venous vascular access with two plug units.

FIG. 20 shows another example embodiment of the housing of the device for monitoring B the arterial and venous vascular access, which differs from the embodiment described by reference to FIG. 6 by the fact that, in place of a plug unit 35 with two plugs 35A, 35B lying beside one another, two plug units 35 and 35' with, respectively, two plugs 35A, 35B are provided. The parts corresponding to one another are provided with the same reference numbers. Additional plug unit 35' permits the connection of a further detection device 40 to evaluation unit 41 of monitoring device B with socket unit 36 shown in FIG. 7A and FIG. 7B.

Figures 21A, 21B:
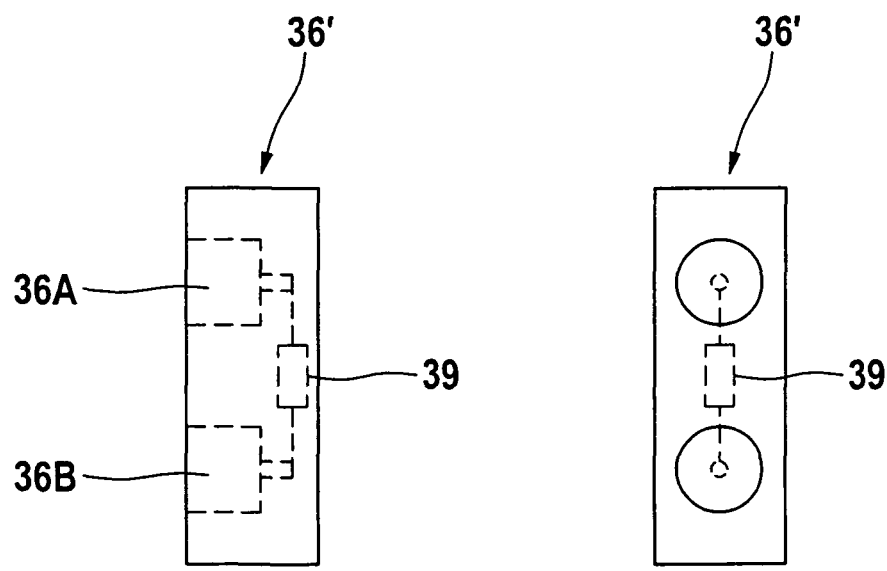
FIGS. 21A and 21B show a protective cap for a free plug unit.

In the event that only one detection device 40 is to be connected to evaluation unit 41, the plug unit which is not connected to a socket unit can be closed with a protective cap, which forms an insulating protection for the contacts. FIGS. 21A and 21B show an example embodiment of protective cap 36', which is constituted like socket unit 36 of FIGS. 7A and 7B. The two sockets 36A, 36B of protective cap 36' are connected to a resistor 39, the electrical resistance whereof corresponds to the electrical resistance of an intact detection device 40. It is however also possible not to provide such a terminating resistor in the protective cap.

Evaluation unit 41 can be designed in such a way that, before the treatment is carried out, the electrical resistance between the plugs and sockets of plug-socket unit 35, 36 is measured and the measured resistance is compared with a setpoint value for the resistance, which corresponds to the terminal resistance of an intact detection device 40. If the measured value for the resistance diverges from the setpoint value by a preset amount, evaluation unit 41 concludes that detection device 40 is defective.

A preferred embodiment makes provision such that the user can preselect at the start of the treatment whether the monitoring is to take place with one or two detection devices. In a first embodiment, monitoring device B comprises an input unit 41A, on which it is possible to input whether one or two detection devices are to be used. For this purpose, the user may be prompted by a signal unit (not shown). The evaluation unit can also be constituted in such a way that, after the input, a check is made to establish whether one or two detection devices are in fact connected. In an alternative embodiment, the input unit (not shown) of the blood treatment apparatus is used to input whether one or two detection devices are being used.

Figure 22:
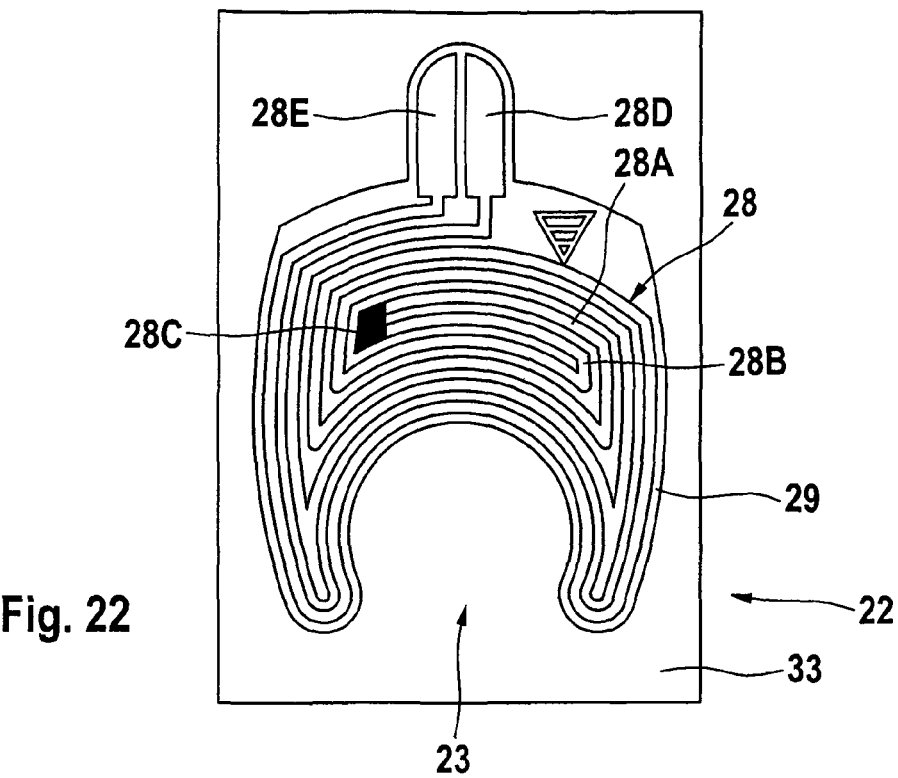
FIG. 22 shows a further example embodiment of the detection device.

FIG. 22 shows a further embodiment of the device for the detection of fluid, which differs from the previously described embodiments by the layout, wherein the parts corresponding to one another are again provided with the same reference numbers. Moisture sensor 28 again comprises two strip conductors 28A, 28B, which lead from contact elements 28D and 28E to a terminating resistor 28C, which is again printed on the carrier material. The example embodiment of FIG. 22 is characterized in that cutout 23 for the puncture needle does not lie in the center of pad 22, so that the cutout is not completely surrounded by the pad. Pad 22 which surrounds the cutout only over a part of the periphery enables a particularly easy application of the pad to an already punctured patient access. A fixing means for fixing the needle is dispensed with in the case of this embodiment.

In the example embodiment of FIG. 22, carrier material 29 of pad 22 is applied with an adhesive layer 32 onto a silicone paper 33, which is larger than the carrier material of pad 22 (FIG. 4). In this example embodiment, silicone paper 33 is a rectangular liner paper, which projects on all sides over the outer edge of the carrier material. By bending the projecting edges, carrier material 29 can easily be pulled off from silicone paper 33. The pulling-off of the carrier material is also facilitated by the fact that the area on which contact elements 28D, 28E are applied is constituted as a tab, which preferably lies opposite the cutout, but can also be provided on another side. One or more pull-off tabs without contact elements can however also be provided.

Instead of a silicone paper, use may also be made of so-called liners made of other materials, by means of which the carrier material can easily be pulled off.

Figure 23:
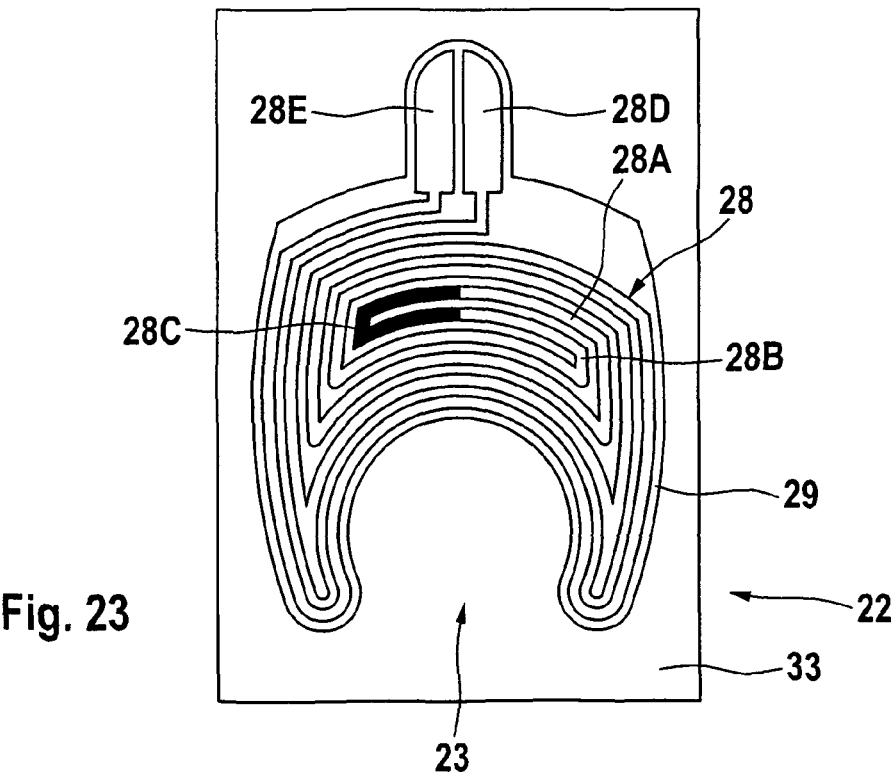
FIG. 23 shows a further example embodiment of the detection device.

FIG. 23 shows an example embodiment of detection device 40, which differs from the embodiment of FIG. 22 solely in that terminating resistor 28C is applied as an elongated extensive structure, as a result of which a smaller production-related spread of the electrical resistance is achieved. This elongated extensive structure may be constituted as a section of the printed-on strip conductor. The width of this structure may correspond to the width of the strip conductor.

The invention claimed is:

1. A device for detecting moisture for use with a device for monitoring an access to a patient for an apparatus with which a fluid can be at least one of (a) fed to a patient and (b) carried away from a patient via a hose line, the device for detecting moisture comprising:
 a cover made of a flexible material and configured to be placed onto the patient's skin, the cover including
  an upper side configured to face away from the patient's skin when the cover is placed onto the patient's skin and
  an underside configured to face the patient's skin when the cover is placed onto the patient's skin, and
  a cutout configured to allow passage there through of a cannula for the patient access and a moisture sensor with contact elements for connecting the moisture sensor, Wherein the cover is impermeable to liquid at the underside, and permeable to liquid at the upper side.

2. The device for detecting moisture according to claim 1, wherein the device for detecting moisture is configured to be operated in connection with a device for monitoring the vascular access in an extracorporeal blood treatment, in which a patient's blood is carried away from the patient via an arterial hose line which has an arterial cannula, and is fed back to the patient via a venous hose line which has a venous puncture cannula.

3. The device for detecting moisture according to claim 1, wherein the cover is permeable to air and water vapor at the underside.

4. The device for detecting moisture according to claim 1, wherein the cover is a pad with two longitudinal sides and two narrow sides.

5. The device for detecting moisture according to claim 1, wherein the cutout in the cover is a substantially circular or oval cutout.

6. The device for detecting moisture according to claim 1, wherein the cover comprises a first predetermined rupture line, which extends from the cutout in the cover to an edge of the cover.

7. The device for detecting moisture according to claim 1, wherein the cover comprises a flexible carrier material, wherein at least one strip conductor made of a flexible material and at least two contact elements for connecting the at least one strip conductor are applied on an upper side of the carrier material.

8. The device for detecting moisture according to claim 6, wherein the cover comprises a second predetermined rupture line, the second predetermined rupture line dividing the cover into two sections, the moisture sensor being disposed in one of the two sections of the cover.

9. The device for detecting moisture according to claim 8, wherein the carrier material is a nonwoven fabric.

10. The device for detecting moisture according to claim 9, wherein the nonwoven fabric has a thickness of 50 to 500 µm, preferably 100 to 200 µm, in particular 150 µm.

11. The device for detecting moisture according to claim 9, wherein the nonwoven fabric has a thickness of 100 to 200 µm.

12. The device for detecting moisture according to claim 11, wherein the nonwoven fabric has a thickness of 150 µm.

13. The device for detecting moisture according to claim 7, wherein the at least one strip conductor is printed on the carrier material.

14. The device for detecting moisture according to claim 7, wherein the at least one strip conductor has a layer thickness of 10 to 150 µm, preferably 50 to 100 µm.

15. The device for detecting moisture according to claim 7, wherein the at least one strip conductor has a layer thickness of 50 to 100 µm.

16. The device for detecting moisture according to claim 7, wherein the at least one strip conductor is made from a conductive flexible material which is screen-printed on the upper side of the carrier material.

17. The device for detecting moisture according to claim 7, wherein the at least one strip conductor comprises a first strip conductor leading to a terminating resistor and a second strip conductor leading away from the terminating resistor, ends of the first and second strip conductor being connected electrically to the contact elements applied on the carrier material.

18. The device for detecting moisture according to claim 17, wherein the at least one strip conductor further comprises a third strip conductor leading to a second terminating resistor and a fourth strip conductor leading away from the second terminating resistor, ends of the third and fourth strip conductors being electrically connected to the contact elements applied on the carrier material.

19. The device for detecting moisture according to claim 17, wherein the first or second terminating resistor is printed on the carrier material.

20. The device for detecting moisture according to claim 7, wherein the at least one strip conductor forms at least one conductor loop at least partially surrounding the cutout in the cover.

21. The device for detecting moisture according to claim 1, wherein the cover further includes an adhesive layer at the underside of the cover, so that the cover is adhesively fixable to the patient's skin.

22. The device for detecting moisture according to claim 21, wherein the adhesive layer is impermeable to liquid.

23. The device for detecting moisture according to claim 21, wherein the adhesive layer extends only over a section of the underside of the cover, so that another section of the underside of the cover is free from the adhesive layer.

24. The device for detecting moisture according to claim 23, wherein the section of the cover free from the adhesive layer is the region of the cover on which the contact elements for the at least one strip conductor are disposed.

25. A device for monitoring an access to a patient for an apparatus with which a fluid is fed to the patient or carried away from the patient via a hose line, the device for monitoring an access comprising:
 a device for detecting moisture according to claim 1.

26. The device for monitoring an access to a patient according to claim 25, wherein the device is configured to monitor a vascular access of an extracorporeal blood treatment apparatus in which a patient's blood is carried away from the patient via an arterial hose line which has an arterial cannula and is fed back to the patient via a venous hose line which has a venous puncture cannula.

27. The device for monitoring an access to a patient according to claim 25, further comprising:
an evaluation unit connectable to the moisture sensor of the device for detecting moisture.

28. The device for monitoring an access to a patient according to claim 27, further comprising: a connection cable for producing a connection between the moisture sensor and the evaluation unit, wherein the connection cable includes a connection part with spring-loaded contacts which are electrically connectable to contact elements of the moisture sensor.

29. The device for monitoring an access to a patient according to claim 27, wherein the evaluation unit comprises a unit for determining the resistance or the capacitance between the contact elements of the moisture sensor.

30. The device for monitoring an access to a patient according to claim 25, further comprising:
a transmitting unit connected to the evaluation unit; and
a receiving unit spatially separated from the transmitting unit.

31. A blood treatment apparatus with an extracorporeal blood circuit, the blood treatment apparatus comprising:
an arterial hose line with an arterial cannula and
a venous hose line with a venous cannula, and
the device for monitoring an access according to claim 25, the device for monitoring an access being configured to monitor at least one of (a) an arterial vascular access and (b) a venous vascular access.

32. The blood treatment apparatus according to claim 31, further comprising:
a control unit, wherein the device for monitoring an access cooperates with the control unit of the blood treatment apparatus in such a way that at least one of (a) a control signal for triggering an alarm and (b) an intervention into the machine control is generated if moisture is detected by the device for detecting moisture.

* * * * *

UNITED STATES PATENT AND TRADEMARK OFFICE
CERTIFICATE OF CORRECTION

PATENT NO. : 8,454,550 B2  Page 1 of 1
APPLICATION NO. : 13/201593
DATED : June 4, 2013
INVENTOR(S) : Koenig et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 151 days.

Signed and Sealed this
Eighth Day of September, 2015

Michelle K. Lee
*Director of the United States Patent and Trademark Office*